US006540991B2

(12) United States Patent
Klassen et al.

(10) Patent No.: US 6,540,991 B2
(45) Date of Patent: Apr. 1, 2003

(54) STABILIZED ACTIVE MATERIALS

(75) Inventors: Darryl F. Klassen, London (CA); David J. Muir, Dorchester (CA)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/828,040

(22) Filed: Apr. 6, 2001

(65) Prior Publication Data

US 2002/0146387 A1 Oct. 10, 2002

(51) Int. Cl.⁷ .................. A01N 31/08; A01N 25/00; A01N 25/28; A01N 35/02; A01N 37/06
(52) U.S. Cl. .................. 424/84; 424/451; 424/457; 424/538; 424/546; 514/734; 514/963; 514/964; 514/970; 514/972; 514/546; 514/698; 514/703; 514/739
(58) Field of Search .................. 424/84, 451, 457, 424/538, 546; 514/734, 963, 964, 970, 972, 546, 698, 703, 739

(56) References Cited

U.S. PATENT DOCUMENTS

| | | | |
|---|---|---|---|
| 3,516,941 A | 6/1970 | Matson ..................... 264/4.33 |
| 3,577,515 A | 5/1971 | Vandegaer ................. 424/497 |
| 3,691,140 A | 9/1972 | Silver ......................... 526/240 |
| 4,325,941 A | * 4/1982 | Dal Moro et al. ............ 424/84 |
| 4,402,856 A | 9/1983 | Schnoring et al. ..... 428/402.22 |
| 4,439,488 A | 3/1984 | Trimnell et al. ....... 428/402.24 |
| 4,487,759 A | 12/1984 | Nesbitt et al. .............. 424/497 |
| 4,663,315 A | 5/1987 | Hasegawa et al. |
| 4,689,293 A | 8/1987 | Goosen et al. .............. 435/182 |
| 4,755,377 A | 7/1988 | Steer ......................... 424/76.4 |
| 4,785,107 A | 11/1988 | Helwig et al. .............. 546/244 |
| 4,911,928 A | 3/1990 | Wallach .................... 428/402.2 |
| 4,968,487 A | * 11/1990 | Yamamoto et al. ......... 422/125 |
| 5,045,569 A | 9/1991 | Delgado ..................... 521/60 |
| 5,189,088 A | 2/1993 | Wang et al. ................ 524/222 |
| 5,326,847 A | 7/1994 | Burleigh et al. ............. 528/60 |
| 5,364,969 A | 11/1994 | Sakurada et al. ........... 568/421 |
| 5,508,313 A | 4/1996 | Delgado et al. ............. 521/63 |
| 5,635,609 A | 6/1997 | Levy et al. .................. 536/2 |
| 5,645,844 A | 7/1997 | Henderson et al. ......... 424/405 |
| 6,080,418 A | 6/2000 | Sengupta et al. ........... 424/408 |
| 6,252,106 B1 | 6/2001 | Yamamoto et al. ......... 560/261 |

FOREIGN PATENT DOCUMENTS

| | | |
|---|---|---|
| CA | 1179682 | 12/1984 |
| DE | 41 36 832 A1 | 5/1992 |
| EP | 0 376 888 | 12/1989 |
| EP | 0 371 635 B1 | 7/1996 |
| GB | 1371179 | 10/1974 |
| JP | S-60-252403 | 5/1984 |
| JP | 59-095206 | 6/1984 |
| JP | 5-000909 | 1/1993 |
| JP | H-9-1244-08 | 11/1995 |
| WO | WO 99/56541 | 11/1999 |

OTHER PUBLICATIONS

Hill et al., "Sex Pheromone Components of the Omnivorous Leafroller Moth, Platynota," *J. Chem. Ecol.*, vol. 1, No. 1, pp. 91–99 (1975).
Database CROPU Online retrieved from STN–International Database accession No. 1999–81443 CROPU, XP002206570, controlled terms, "CT" extended abstract "ABEX"& JP 10 279402A (Earth Seyaku) Oct. 20, 1998 (Oct. 20, 1998).
Database CA Online, Chemical Abstracts Service, Columbus, Ohio, US, J.G. Millar: "Degradation and stabilization of E8, E10–dodecadienol, the major component of the sex pheromone of the codling moth (Lepidoptera Tortricidae)" retrieved from STN–International Database accession No. 123:308636 CA XP002206571 abstract, & J.Econ.Entomol., vol. 88, No. 5, 1995, pp. 1426–1432.
Database WPI, Section Ch, Week 199615 Derwent Publications Ltd., London, GB; Class C02, AN 1996–146869 XP002206572 & JP 08 034705 A (Katsuta S), Feb. 6, 1996 (Feb. 6, 1996) abstract.

* cited by examiner

*Primary Examiner*—John Pak
(74) *Attorney, Agent, or Firm*—Dale A. Bjorkman

(57) ABSTRACT

A stabilized insect mating disruption pheromone compositions comprising an insect pheromone and 2,2'-Methylenebis(6-t-butyl-p-cresol). Methods of use and microcapsules containing these compositions are also provided.

20 Claims, No Drawings

STABILIZED ACTIVE MATERIALS

TECHNICAL FIELD

This invention relates to stabilized active materials. Particularly, the invention relates to the stabilization of insect pheromones.

BACKGROUND OF THE INVENTION

Methods of eliminating unwanted pests from orchards, crops and forests frequently entail the use of organophosphate insecticides. Alternative methods involve insect mating disruption, where insect pheromones are used to control pests in any desired location, including protecting agricultural crops and forestry. In insect mating disruption methods, the mating pheromone plume of a female insect is typically masked with other pheromone point sources. This reduces the likelihood of a male insect finding a female, and subsequently disrupts and reduces larvae production. The insect population of the next generation is thus decreased, as well as potential crop damage.

Stabilization methods for insect pest pheromones are known, such as described in U.S. Pat. No. 5,364,969 (Sakurada et al). Sakurada et al describe admixing the sex pheromone compound with a specified amount of (a) a specific phenolic compound, e.g. tert-butyl hydroquinone, di-tert-butyl hydroquinone, di-tert-amyl hydroquinone, di-tert-buytl p-cresol, methyl hydroquinone and p-methoxy phenol, as an antioxidant and (b) 2-(2'-hydroxy-3'-tert-butyl-5'-methyl phenyl)-5-chlorobenzotriazole in combination.

The need still exists to stabilize an insect pheromone to ensure efficacy over the typical mating season of the insect pests.

SUMMARY OF THE INVENTION

This invention relates to a method of stabilizing an insect pheromone composition using 2,2'-Methylenebis(6-t-butyl-p-cresol), CAS No. 119-47-1. The present invention also relates to an insect pheromone composition comprising a pheromone and 2,2'-Methylenebis(6-t-butyl-p-cresol).

Another aspect of the present invention relates to a composition further comprising a benzotriazole, and in preferred cases, 2-(2'-hydroxy-3',5'-di-tert-amyl-phenyl) benzotriazole.

Yet, another aspect of the present invention relates to a method of protecting a crop against insect pests by applying a microcapsule comprising an insect pheromone, and 2,2'-Methylenebis(6-t-butyl-p-cresol).

DETAILED DESCRIPTION OF THE INVENTION

The present invention provides a composition that is stabilized to provide extended release of the insect pheromone over a typical flight season for insect pests. Typically, a generation of Lepidopteran insects averages approximately 6 weeks. Thus, a sustained release period of at least 6 weeks for the particular insect pheromone would provide for effective disruption of the insect pest mating during its flight period when the pheromone is introduced into the intended environment.

A stable insect pheromone composition allows for a reduced frequency of application. A pheromone that is effective throughout an entire generation of an insect pest eliminates the need for subsequent applications to ensure mating disruption of the insect pests.

Because the insect pheromone can be provided in a stabilized format, a long lasting delivery system may be engineered to provide slow release over a long duration of time. The stabilized format allows for a slow release from a single application without spiking as may be obtainable from multiple applications. "Spiking" as used herein may be triggered by instantaneous or short-term release of the active agents from the shell. Since a mating cycle of a given insect pest may last up to 4–6 weeks in length, the slow release of an insect pheromone may be desirable to provide effective control of insect mating over the duration. Thus, the present invention may be used to control the release rate of insect pheromones thereby effectively controlling and disrupting the mating behavior of the species in a particular intended environment. For example, an insect pheromone for codling moth can be made to steadily dissipate into the intended environment over the duration of a mating cycle for codling moth. A typical duration for a nonstabilized codlemone, the insect pheromone for the codling moth is less than 1 week, as against about 6 weeks for codlemone stabilized according to the present invention.

A stabilized composition of insect pheromone according to the present invention comprises 2,2'-Methylenebis(6-t-butyl-p-cresol). Insect pheromones stabilized using 2,2'-Methylenebis(6-t-butyl-p-cresol) alone, or in combination with additional stabilization agents, show remarkable efficacy over an extended period of time. The term "efficacy" as used in the present invention relates to the stability of the insect pheromone in showing mating inhibiting effect over a period of time. A preferable duration of mating inhibiting may be greater than 4 weeks, more preferably greater than 6 weeks, and most preferably greater than 8 weeks.

The stabilizer of the present invention may preferably be combined with UV absorbers including, but not limited to benzotriazoles, hindered amine light stabilizers (HALS), cinnamate esters, hydroxybenzophenones, and oxanilides. Typical benzotriazoles usable in the present invention include 2-(2'hydroxy-3',5'-tert-amylphenyl)benzotriazole; 2-(2'-hydroxy-3'-tert-butyl-5'-methylphenyl)-5-chloro-benzotriazole; and the like. Additional stabilizers may also be incorporated, such as nickel and sulfur containing quenchers and hydroperoxide/peroxide scavengers. UV absorbers as used in the present invention relate to chemical additives used to improve the stability of the insect pheromone against ultraviolet degradation.

UV blockers may also be combined with the stabilizer of the present invention. Typical UV blockers such as carbon black and titanium dioxide are usable.

Other antioxidants are also usable to provide a stabilized insect pheromone of the present invention such as those in the family of sterically hindered phenols, bisphenols, aminophenols, secondary aromatic amines, hydroxybenzyl compounds, alkyl and arylthioethers, thiobisphenols, phosphites and phosphonites, and zinc-thiocarbamates, and the like.

Preferred ratios of insect pheromone to 2,2'-Methylenebis(6-t-butyl-p-cresol) may be in the range between 200:1 and 0.5:1; more preferably between 50:1 and 0.5:1; and most preferably in the range between 20:1 and 1:1. Preferred ratios of insect pheromone to UV absorber in the composition may be in the range between 200:1 and 0.5:1; more preferably between 50:1 and 0.5:1; and most preferably in the range between 20:1 and 1:1.

Pheromones may be defined as compounds which, when naturally produced, are secreted by one member of an animal species which can influence the behavior or development of another member of the same animal species. Pheromones are species-specific and therefore the application of pheromones for insect behaviour modification has minimal effect on non-target pests. Pheromones supplied for modification of insect behavior interfere with the "mate finding process" by releasing point sources of pheromone, which may compete with or camouflage the pheromone plume of a female of the same species. This latter type of action differs from chemical insecticides or insect growth regulators or hormones, in that pheromones target future generations of insects, not present ones. As pheromones are very species-specific and are used only in small quantities, their use is more environmentally acceptable than broadcasting pesticides.

Pheromones useful in the invention are preferably insect pheromones. In describing the structure of the pheromone, the following notation is used: the type (E (trans)or Z(cis)) and position of the double bond or bonds are given first, the number of carbon atoms in the chain is given next and the nature of the end group is given last. To illustrate, the pheromone Z-10 C19 aldehyde has the structure;

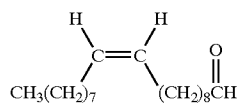

Pheromones can be mixtures of compounds with one component of the mixture predominating, or at least being a significant component. Predominant components of insect pheromones, with the target species in brackets, include, for example: E/Z-11 C14 aldehyde (Eastern Spruce Budworm), Z-10 C19 aldehyde (Yellow Headed Spruce Sawfly), E,E-8,10 C12 alcohol (Codling moth), E-11 C14 alcohol/acetate (Tufted Apple Budmoth), E-11 C14 acetate (Sparganothis Fruitworm), Z-11 C14 acetate (Blackheaded Fireworm), Z-9 C12 acetate (Grape Berry Moth), Z-11 C14 acetate (Leafroller), E/Z-4 C13 acetate (Tomato Pinworm), Z, Z/Z, E-7,11 -C16 acetate (Pink Cotton Bullworm), Z-8-C12 acetate (Oriental Fruit Moth), Z/Z-3,13 C18 acetate (Peach Tree Borer), E,Z/Z,Z-3,13-C18 acetate (Lesser Peach Tree Borer), and 7,8-Epoxy-2-methyl-C18 (Gypsy Moth), among others.

An example of a ketone that is a pheromone is E or Z 7-tetradecen-2-one, which is effective with the oriental beetle. An ether that is not a pheromone but is of value is 4-allylanisole, which can be used to render pine trees unattractive to the Southern pine beetle.

Stabilized insect pheromones according to the present invention may be provided in any delivery vehicle appropriate for the intended environment. Examples of such delivery vehicles include microcapsules, microbeads, plastic laminate flakes and larger mechanical devices such as hollow fibres and twist ties.

Microcapsules may be formed for example using conventional polyurea and/or polymethyleneurea encapsulation techniques such as what is taught in U.S. Pat. No. 3,516,941 (Matson), U.S. Pat. No. 3,577,515 (Vandegaer), and U.S. Pat. No. 4,487,759 (Nesbitt et al). Alternatively, microcapsules having gelatin shells may be used in the microbeads of the invention and prepared by the methods provided in U.S. Pat. No. 4,402,856. In another embodiment, microcapsules may alternatively be provided in the form of a liposome, and prepared by the processes taught in U.S. Pat. No. 4,911,928. Other examples of microcapsules are disclosed in U.S. Pat. Nos. 3,691,140; 5,045,569; and 5,508,313 as well as European Patent Application 371,365, all of whose teachings are incorporated here by reference.

United Kingdom Patent No. 1,371,179 also discloses the preparation of polyurea capsules for containing dyes, inks, chemical reagents, pharmaceuticals, flavoring materials, fungicides, bactericides and pesticides such as herbicides and insecticides. Particle sizes as low as one (1) micron are exemplified. Encapsulation of insect hormones and mimics are among the systems mentioned.

Canadian Patent No. 1,179,682 discusses encapsulation of pheromones. Microcapsules containing pheromones are produced from toluene diisocyanate and ethylene diamine and/or diethylene triamine.

The microcapsules of the present invention may optionally also have adherent coatings to aid the microcapsule to adhere to the intended environment, especially when the microcapsules are used for agricultural purposes. Examples of adherent coatings include tacky microspheres of adhesives. The tacky microspheres have sufficient adhesive properties to provide the desired adhesive function, and do not present a danger of completely coating the microcapsule and possibly inhibiting the release characteristics of the particle. Preferably, the adhesive material is an acrylate or methacrylate-based adhesive system comprising infusible, solvent dispersible, solvent insoluble, inherently tacky elastomeric copolymer microspheres as disclosed in U.S. Pat. No. 3,691,140 to Silver, as well as those disclosed in U.S. Pat. No. 5,045,569 to Delgado, and U.S. Pat. No. 5,508,313 to Delgado et al. Other types of adhesive usable in the present invention include adhesive latex such as Companion™ and Rhoplex™, available from Rohm & Haas Company, Philadelphia, Pa.; DPI S-100™, available from Deerpoint Industries of Hawthorn Woods, Ill.

Microbeads comprise a matrix forming material, and are preferably substantially spherical. The matrix forming materials of the microbead core are hydrophilic and water soluble. Entrained or finely dispersed within the matrix are micro-sized droplets of active material such as insect pheromone. Insect pheromones that can be immobilized within the hydrogel microbeads include acetates, aldehydes, alcohols, esters, epoxy compounds, ethers, and ketones, especially reactive ketones in which the double bond of the carbonyl group is conjugated with one or more double bonds, for example acetophenone where the carbonyl group is conjugated with double bonds of the aromatic ring. Examples of microbeads are disclosed in U.S. Pat. Nos. 4,689,293; 4,755,377; and 5,645,844.

In view of the increasing awareness of insecticide toxicity to humans and other environmental concerns, it would be advantageous to provide an insect pheromone delivery system having an extended release life and having a hydrogel material in order that it be non-toxic and bio-degradable. It would also be advantageous to provide a system for sprayable long lasting insect pheromone delivery that would be applicable to a broad spectrum of insect pheromones thereby eliminating the issue of reactivity of the insect pheromone with one of the membrane components.

Advantageously, the hydrogel matrix core is preferably made from environmentally or biologically friendly materials to provide sufficient immobilization of oil soluble insect pheromones such that the insect pheromone can be delivered and sprayed by conventional techniques. By utilizing a hydrophilic matrix core, the hydrogel microbeads entrap micro-sized droplets of insect pheromone within the matrix. This is in contrast to delivery systems that solely utilize micro by interfacial polymerization. Immobilizing insect pheromone in a hydrophilic matrix core advantageously imparts the capability of the hydrogel microbeads to immobilize oil-soluble insect pheromones and minimizes the risk of undesired reactivity between the insect pheromone and its immobilizer. Thus, immobilization of insect pheromones by use of the microbeads of the invention does not render the immobilized material inert or ineffective.

In the presence of humidity, the hydrogel microbeads are surprisingly found to be capable of absorbing moisture, rehydrating, and consequently releasing insect pheromone contained within the microbead. This behavior can be cyclical. Thus, by controlling the humidity (or dryness) of the ambient air, the release rate of insect pheromone from the microbeads can be controlled such that specific periods of release can be generally predicted. It is therefore possible to release the insect pheromone on demand from the microbead. Release on demand, or "smart release," can be advantageous in those instances where release is preferred at certain times. The microbeads' ability to release more insect pheromone out from the matrix may increase the longeveity of the release period. Preferably, the microbeads are delivered to an intended environment in effective amounts to obtain the desired effect. For example, microbeads having pheromones entrained therein, are preferably delivered to a desired area in amounts such that mating disruption is effected and release is accomplished for more than 4 weeks, more preferably, the microbead can release for more than about 6 weeks; and most preferably more than about 8 weeks.

Typically, each microcapsule of the present invention has an insect pheromone or pheromones encapsulated or retained in it. The pheromones may be employed in combination with other chemicals and/or materials used to facilitate the effectiveness of the microcapsules in their intended environment. In an embodiment to protect against the Leafroller species of pests, and in particular the Redbanded Leafroller (*Argyrotaenia velutinana*), the insect pheromone effective for their control consists of 88:12 ratio of Z-11-Tetradecenyl Acetate to E-11-Tetradecenyl Acetate.

The insect pheromone of the present invention may be delivered in any manner appropriate for use in the intended environment. Most preferably, the insect pheromone of the present invention may be provided in microencapsulation form.

Conventional sprayable pheromone formulations are generally provided in liquid filled microcapsules containing an insect pheromone. Typically, the microcapsules have a polyurea membrane that can be formed using an interfacial process involving an isocyanate and an amine. Microencapsulation by this method has been described for example in U.S. Pat. No. 4,487,759 (Nesbitt et al). These polyurea membranes allow insect pheromones to be released into the atmosphere for up to a total of 2–3 weeks for most insect pheromones.

For spraying applications, particularly aerial spraying, it is desirable that the microbeads be capable of remaining suspended in solution (e.g., water) to ensure that the microbeads do not sink, settle, or coagulate in the suspension. A uniform suspension ensures an even spray coverage. Preferably, the microbeads are able to remain in suspension, thus minimizing if not eliminating the need to agitate during application (and storage). Various suspension aids can also be included in the suspension containing the microbeads. Examples of suitable suspension aids include rhamsam gum, xanthum gum, gellan gum, pectin, and gum arabic.

Owing to the handling to which the microbeads are subjected, it is desirable that the microbeads should be somewhat elastic, and not frangible. For example, typical atomization of a suspension during a spray application will force the suspension through two rotating perforated discs that are immediately upstream of the discharge nozzle. Sufficient elasticity of the microbeads minimizes physical damage to the microbeads as they pass through the discs.

The microcapsules may be delivered to the intended environment by methods as are known in the art, such as spraying. Preferably, the microcapsules of the present invention should remain in suspension in water or any suitable solution. A suspension aids the delivery by preventing the microcapsules from sinking and coagulating before spraying. It is preferable to reduce this settling process, although it can be restored to some extent by agitation, the necessity of which is one disadvantage.

Use of interfacial polymerization to encapsulate substances such as pharmaceu-ticals, pesticides and herbicides is taught in U.S. Pat. No. 3,577,515. The encapsulation process involves two immiscible liquid phases (typically water and an organic solvent), one being dispersed in the other by agitation, and the subsequent polymerization of monomers from each phase at the interface between the bulk (continuous) phase, and the dispersed droplets. Polyurethanes and polyureas are materials suitable for producing the microcapsules. The microcapsules comprise a polymeric sphere and a liquid center, ranging from 30 micron to 2 mm in diameter, depending on monomers and solvents used.

Highly viscous and thickened hydrogels have been used to deliver pheromones, fragrances and other water-insoluble insect pheromones. U.S. Pat. No. 4,755,377, for example, describes a process of encapsulating perfume or fragrant material within an aqueous-based gel composition. The resulting material is in the form of a highly viscous semi-solid. U.S. Pat. No. 5,645,844 describes the use of chitosan paste for delivery of pheromones to disrupt insect mating, where the material can be dispensed by an apparatus such as a caulking gun.

Most hydrogels are safe and non-toxic to humans. Hydrogels have been used for the encapsulation of biological materials whereby the formulation is non-lethal to the viability of the cells, proteins, and related materials. U.S. Pat. No. 4,689,293 describes the process of encapsulating living tissue or cells in alginate beads. The encapsulation shell permits the passage of materials and oxygen to the cells and permits the diffusion of the metabolic by-products from the gel. In U.S. Pat. No. 5,635,609, the encapsulation art described involves one esterified polysaccharide (i.e., alginate) and one polyamine (i.e. chitosan) whereby the outer surface membranes are formed through covalent amide bonds. U.S. Pat. No. 4,439,488 teaches a process of encapsulating pheromone whereby the biological agents are dissolved or dispersed in an aqueous paste of a gel-forming polyhydroxy polymer. By adding boric acid to an aqueous solution at alkaline pH, the paste transforms into a gel thereby entrapping the agents in a protective matrix.

Japanese patent S 60-252403 describes a method of forming sprayable, slow release pheromone agent obtained by emulsification co-polymerization. In Japanese patent H-9-1244-08, the outer surface of the delivery system (i.e., synthetic resin or inorganic substance) is coated by a waterproof material. The waterproof agent can be a silicon, fluorine, or paraffinic hydrocarbon type material.

Additional vehicles for delivery of the pheromone composition of the present invention include impregnating hollow fibres or twist-ties with a pheromone and then physically attaching the fibres or ties to plants to be protected from insect infestation. This process is labor-intensive and is suitable for protecting small areas, for instance orchards. Another example of a delivery system is plastic laminate flakes that have been impregnated with pheromone. Plastic laminate flakes are dispensed to forests by aerial application, and require special devices for delivery.

All applications and patents cited in this application are incorporated by reference. All parts, percentages and ratios are by weight unless otherwise specified.

What is claimed is:

1. A method of stabilizing an insect pheromone comprising providing a composition, said composition comprising an insert pheromone and an insert pheromone stabilizing amount of 2,2'-Methylenebis(6-t-butyl-p-cresol).

2. The method of claim 1, wherein the composition is preselected for a particular insect pest.

3. The method of claim 1, wherein the composition further comprises a UV absorber.

4. The method of claim 3, wherein the UV absorber is a benzotriazole.

5. The method of claim 3, wherein the UV absorber is selected from 2-(2'hydroxy-3',5'-tert-amylphenyl)benzotriazole and 2-(2'-hydroxy-3'-tert-butyl-5'-methylphenyl)-5-chloro-benzotriazole.

6. The method of claim 3, wherein the UV absorber is selected from the group consisting of hindered amine light stabilizers (HALS), hydroxybenzophenones, cinnamate esters and oxanilides.

7. The method of claim 1, wherein the composition further comprises additional stabilizers selected from nickel and sulfur containing quenchers and hydroperoxide/peroxide scavengers.

8. The method of claim 1, wherein the composition further comprises UV blockers selected from the group consisting of carbon black and titanium dioxide.

9. The method of claim 1, wherein the composition further comprises additional antioxidants selected from the group consisting of sterically hindered phenols, bisphenols, aminophenols, secondary aromatic amines, hydroxybenzyl compounds, alkyl and arylthioethers, thiobisphenols, phosphites and phosphonites, and zinc-thiocarbamates.

10. An insect mating disruption composition comprising an insect pheromone and 2,2'-Methylenebis(6-t-butyl-p-cresol) in an amount effective to stabilize the insect pheromone.

11. The insect mating disruption composition of claim 10, wherein the composition further comprises a UV absorber.

12. The insect mating disruption composition of claim 11, wherein the UV absorber is a benzotriazole.

13. The insect mating disruption composition of claim 11, wherein the UV absorber is selected from 2-(2'hydroxy-3',5'-tert-amylphenyl)benzotriazole and 2-(2'-hydroxy-3'-tert-butyl-5'-methylphenyl)-5-chloro-benzotriazole.

14. The insect mating disruption composition of claim 11, wherein the UV absorber is selected from the group consisting of hindered amine light stabilizers (HALS), hydrobenzophenone, cinnamate esters and oxanilides.

15. The insect mating disruption composition of claim 10, wherein the composition further comprises additional stabilizers selected from nickel and sulfur containing quenchers and hydroperoxide/peroxide scavengers.

16. The insect mating disruption composition of claim 10, wherein the composition further comprises UV blockers selected from the group consisting of carbon black and titanium dioxide.

17. The insect mating disruption composition of claim 10, wherein the composition further comprises additional antioxidants selected from the group consisting of sterically hindered phenols, bisphenols, aminophenols, secondary aromatic amines, hydroxybenzyl compounds, alkyl and arylthioethers, thiobisphenols, phosphites and phosphonites, and zinc-thiocarbamates.

18. A microcapsule comprising an insect pheromone composition of claim 10.

19. A method of controlling an insect pest comprising applying the composition of claim 10 to an environment to be protected in an amount effective to inhibit or disrupt mating of insect pests.

20. The method of controlling an insect pest of claim 19, wherein the insect mating disruption composition is encapsulated in a microcapsule.

* * * * *